(12) United States Patent
Woodburn, III

(10) Patent No.: US 6,945,251 B2
(45) Date of Patent: Sep. 20, 2005

(54) APPARATUS FOR THE STABILIZATION OF HEAD POSITION

(76) Inventor: Robert T. Woodburn, III, 6633 Old Stonehouse Dr., Newburgh, IN (US) 47630

( * ) Notice: Subject to any disclaimer, the term of this patent is extended or adjusted under 35 U.S.C. 154(b) by 271 days.

(21) Appl. No.: 10/072,778

(22) Filed: Feb. 8, 2002

(65) Prior Publication Data

US 2002/0108616 A1 Aug. 15, 2002

Related U.S. Application Data

(60) Provisional application No. 60/267,536, filed on Feb. 9, 2001.

(51) Int. Cl.$^7$ ............................................. A61F 11/00
(52) U.S. Cl. ..................... 128/857; 128/861; 128/859
(58) Field of Search ............................... 128/857, 858, 128/861, 869, 859

(56) References Cited

U.S. PATENT DOCUMENTS

| | | | |
|---|---|---|---|
| 1,795,866 A | * 3/1931 | King ................................ 2/8 |
| 1,986,988 A | * 1/1935 | Treadwell ...................... 128/857 |
| 2,589,504 A | * 3/1952 | Miller .......................... 128/857 |
| 4,841,965 A | 6/1989 | Jacobs |
| 4,971,060 A | 11/1990 | Schneider et al. |
| 4,979,519 A | * 12/1990 | Chavarria et al. ........... 128/857 |
| 5,040,547 A | * 8/1991 | Bergstrom .................... 128/857 |
| 5,090,047 A | 2/1992 | Angotti et al. |
| 5,206,955 A | * 5/1993 | Milligan ............................ 2/9 |
| 5,230,623 A | 7/1993 | Guthrie et al. |
| 5,267,353 A | * 12/1993 | Milligan ............................ 2/9 |
| 5,330,485 A | 7/1994 | Clayman et al. |
| 5,370,117 A | * 12/1994 | McLaurin, Jr. ................ 5/622 |
| 5,464,411 A | 11/1995 | Schulte et al. |
| 5,531,229 A | 7/1996 | Dean et al. |
| 5,566,681 A | * 10/1996 | Manwaring et al. ........... 5/622 |
| 5,588,430 A | 12/1996 | Bova et al. |
| 5,702,406 A | * 12/1997 | Vilsmeier et al. .......... 606/130 |
| 5,706,811 A | 1/1998 | Takeda et al. |
| 5,785,052 A | * 7/1998 | Johnson ....................... 128/830 |
| 5,797,924 A | 8/1998 | Schulte et al. |
| 5,947,981 A | 9/1999 | Cosman |
| 6,096,048 A | 8/2000 | Howard, III et al. |
| 6,143,003 A | 11/2000 | Cosman |
| 6,223,067 B1 | 4/2001 | Vilsmeier et al. |
| 6,523,179 B1 | * 2/2003 | Zegarelli et al. ................... 2/9 |

* cited by examiner

Primary Examiner—Henry Bennett
Assistant Examiner—Camtu Nguyen
(74) Attorney, Agent, or Firm—Jill L. Woodburn

(57) ABSTRACT

An apparatus is provided to fix a thermoplastic mask to a patient. The apparatus includes a member formed to be positioned adjacent a cranio facial bone, a fixation member coupled to the member, and a fastener plate. The fastener plate couples the mask to the fixation member so that the member is in a fixed position relative to the mask.

15 Claims, 17 Drawing Sheets

APPARATUS FOR THE STABILIZATION OF HEAD POSITION

CROSS-REFERENCE TO RELATED APPLICATIONS

This application claims priority to U.S. Provisional Patent Application Ser. No. 60/267,536 filed Feb. 9, 2001.

FIELD OF THE INVENTION

The present invention relates to an apparatus for immobilizing a patient's skull during a medical diagnostic or treatment procedure, and more particularly to an apparatus which permits precise and reproducible positioning of the patient's head and neck during radiation therapy or like medical procedures.

BACKGROUND AND SUMMARY OF THE INVENTION

A variety of medical diagnostic and treatment procedures require that a patient's skull be fixed in an accurate and reproducible position. One example of such a treatment procedure is radiation therapy, which is used to deliver radiation to a target, such as a tumor. An important step in this therapy is treatment planning. To aid in this planning, stereotactic techniques have been developed, which employ accurate and reproducible positioning of the patient's skull during radiographic studies. See, for example, U.S. Pat. No. 5,797,924.

It is also important to immobilize the patient during treatment and radiographic examination in order to assure that radiation is delivered exactly where it is needed and that targets and surrounding normal structures are precisely located. A thermoplastic mask is often used to immobilize the patient's head and ensure reproducibility of the treatment.

According to the present invention, an apparatus is provided that is formed to fix a thermoplastic mask to a patient. The apparatus comprises a member formed to be positioned adjacent to a cranio facial bone of the patient, a fixation member coupled to the member, and a fastener plate. The fastener plate is formed to couple the mask to the fixation member so that the member is in a fixed position relative to the mask.

According to another embodiment of the present invention, an apparatus is provided that is formed to fix a thermoplastic mask to a patient. The apparatus comprises a mouthpiece member, a fixation member coupled to the mouthpiece member, the fixation member including a plate and at least one fastener extending away from the plate, and a fastener plate. The fastener plate is formed for attachment with the at least one fastener so that the mask is coupled between the plate and the fastener plate.

According to another embodiment of the present invention an assembly formed to immobilize a patient's skull during a medical procedure is provided. The assembly comprises a thermoplastic mask and a mouthpiece member coupled to the thermoplastic mask.

According to still another embodiment of the present invention an assembly formed to immobilize a patients skull during a medical procedure is provided. The assembly comprises a thermoplastic mask and an earplug member formed for extension into the auditory canal. The earplug member is coupled to the thermoplastic mask.

According to yet another embodiment of the present invention an assembly formed to immobilize a patient's skull during a medical procedure is provided. The assembly comprises a thermoplastic mask and a nose block member formed to be positioned on a nasal bridge of the patient. The nose block member is coupled to the thermoplastic mask.

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
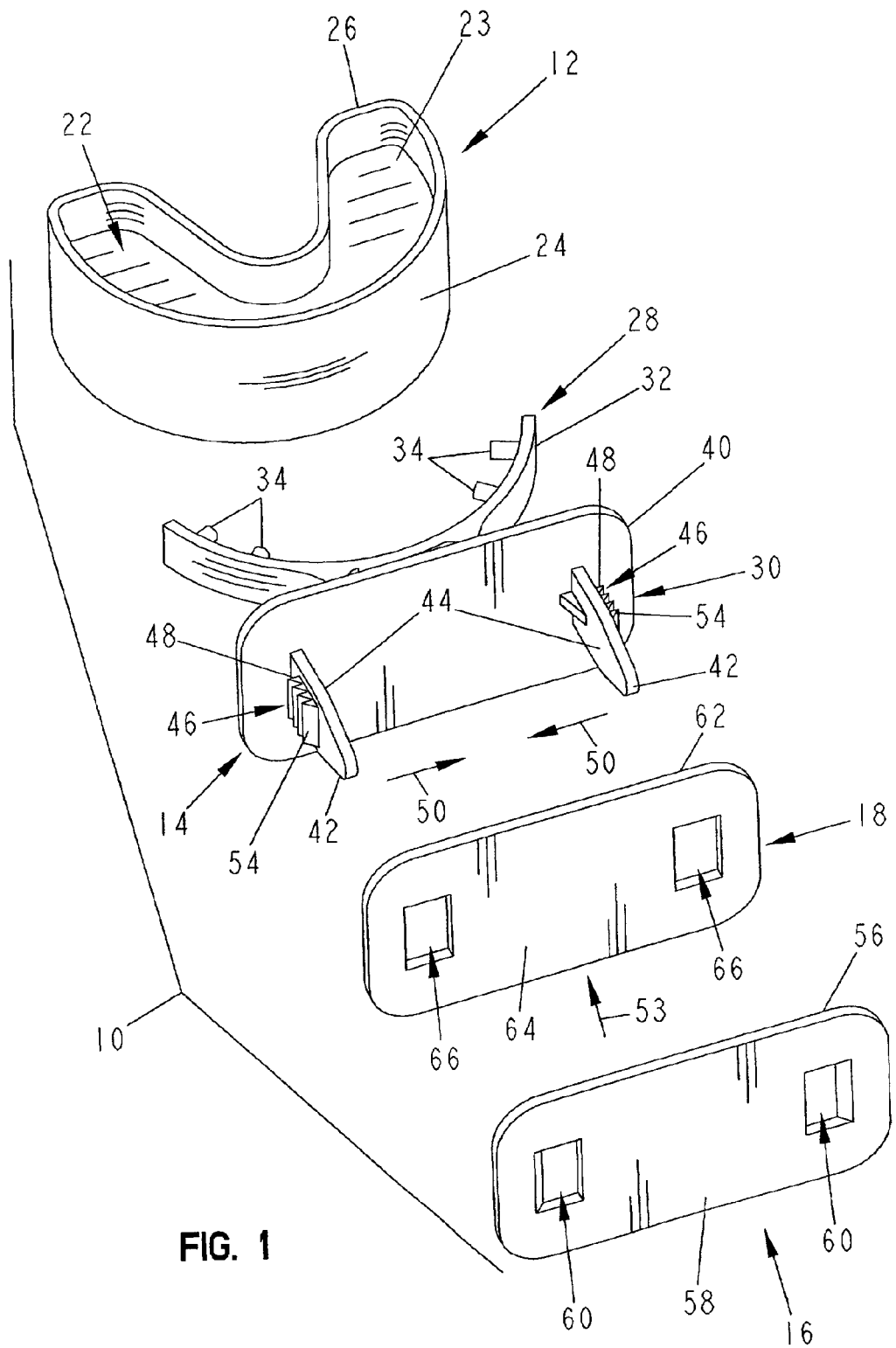
FIG. 1 is an exploded perspective view of the apparatus in accordance with the present invention.

The present invention relates to an apparatus and method for fixing a thermoplastic mask to the head of a patient during medical diagnostic and treatment procedures. The apparatus is formed to press the mask against rigid and fixed portions of the patient's skull in order to maintain a rigid position of the mask relative to the patient's skull. Thus, a patient's head is prevented from moving in the mask. It is appreciated that apparatus 10, 110, 210, 310, 410, 510 as discussed hereafter, may be distributed to a user as a separate apparatus, as part of a kit with a thermoplastic mask 52, or already coupled to the mask 52. Various aspects of the invention are presented in FIGS. 1–17, which are not drawn to scale and wherein like components in the several views are numbered alike.

FIGS. 1–4 illustrate an aspect of the invention in the form of an apparatus 10 that is formed to fix a mask to the fixed cranio facial bones, i.e. maxilla. Apparatus 10 includes a mouthpiece member 12, a fixation member 14 extending from the mouthpiece member 12, a fastener plate 16, and a spacer 18 positioned to lie between the fixation member 14 and the fastener plate 16.

Mouthpiece member 12 is formed from a resinous material that softens when heated. A non-limiting example of a suitable material for forming mouthpiece is ELVAX® 470, an ethylene vinyl acetate copolymer and terpolymer resin, which is commercially available from E.I. DuPont de Nemours, Wilmington, Del. It is appreciated, however that the mouthpiece can also be constructed of a rigid plastic or be a true custom mould, as dentists use in accordance with this disclosure. Mouthpiece member 12 includes a front side 24, a back side 26, and a teeth-receiving portion 22 extending between the front and back sides 24, 26. The receiving portion is defined by an inner surface 23. It is appreciated that the shape of the mouthpiece may vary in accordance with the present disclosure.

Fixation member 14 is coupled to the front side 24 of the mouthpiece member 12 and is formed for attachment to the fastener plate 16. Referring to FIG. 1, the fixation member 14 is generally formed from a rigid plastics material and includes a first end 28 coupled to mouthpiece member 12 and a second end 30 that is formed for attachment with the fastener plate 16. As will be discussed hereafter, fixation member may be formed in a variety of shapes and sizes in accordance with the present invention. It is also appreciated that although the fixation member 14 is illustratively formed of a rigid plastics material, it could be constructed of a variety of materials including metal in accordance with the present disclosure.

Figure 2:
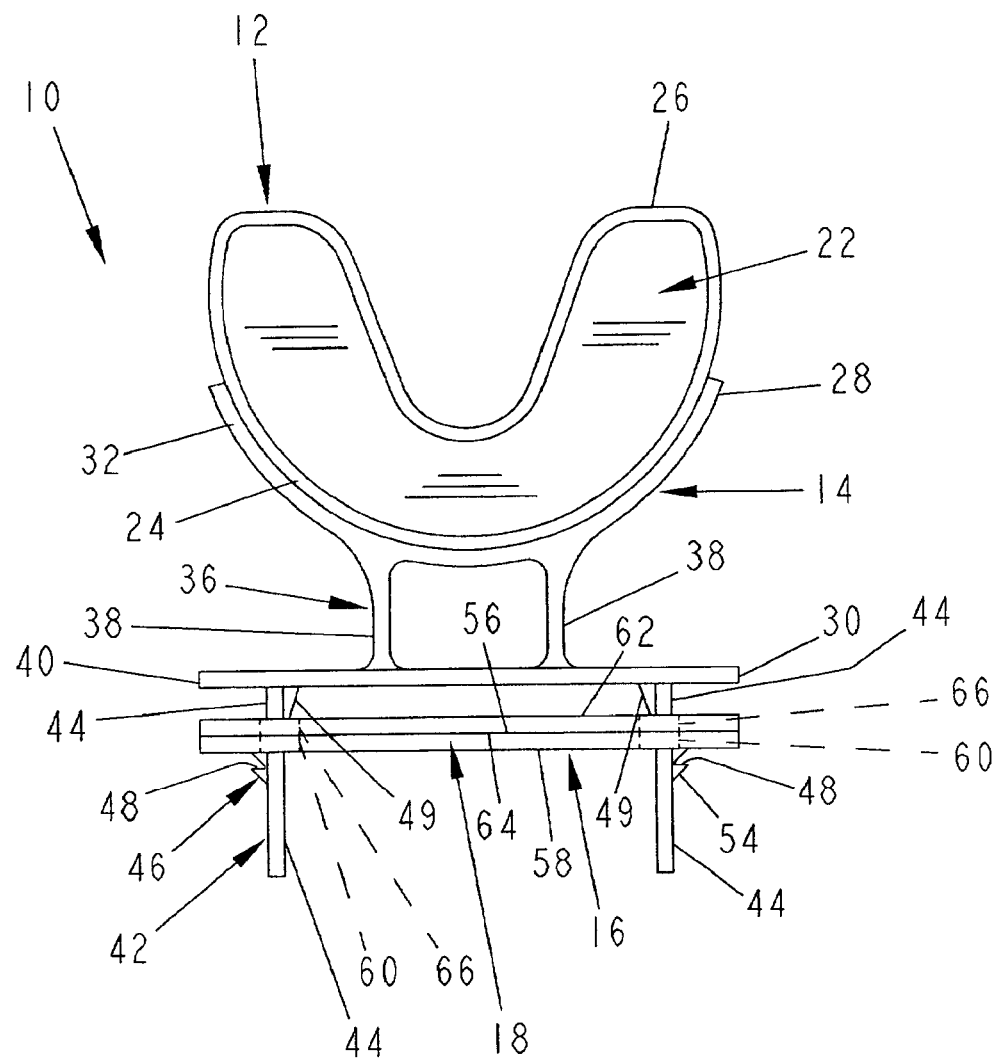
FIG. 2 is a top view of the assembled apparatus of FIG. 1.

As shown in FIGS. 1 and 2, the first end 28 of the fixation member 14 includes an attachment portion 32 that takes the general shape of the mouthpiece member 12. The attachment portion 32 illustratively includes four spaced-apart connectors 34 (FIG. 1) extending away from the first end 28 and toward the mouthpiece member 12. In one aspect of the invention, the connectors 34 are coupled to the mouthpiece member 12 using ultrasonic welding. It is appreciated, however, that the attachment portion 32 of the fixation member 14 may be coupled to the mouthpiece member 12 using any number of commercially available adhesives or with heat welding in accordance with this disclosure.

Referring now to FIG. 2, the first end 28 of the fixation member 14 includes an extension 36 that lies between the attachment portion 32 and the second end 30. The extension 36 illustratively includes two spaced-apart legs 38 that position the second end 28 of the fixation member 14 away from the mouthpiece member 12. The length of the extension 36 is sufficient to position the second end 30 of the fixation member 14 outside of a patient's mouth (not shown) when the mouthpiece member 12 and fixation member 14 are in use. It is appreciated that the shape and length of the extension 36 may vary in accordance with the present disclosure.

As shown in FIG. 2, the second end 30 of the fixation member 14 is spaced-apart from the attachment portion 32 of the first end 28. The second end 30 includes a plate 40 coupled to the extension 36 and fasteners 42 extending from the plate 40. Upon assembly, the fasteners 42 are locked to the fastener plate 16 in order to couple the fixation member 14 and fastener plate 16 together. Illustratively, fasteners 42 are formed as two flexible arms 44 that extend away from the plate 40. Each arm 44 includes a support 49 and four teeth 46 positioned to engage the fastener plate 16. The teeth 46 are configured with faces 48 to engage the fastener plate 16 to couple the fixation member 14 and fastener plate 16 together. The teeth 46 further include ramped surfaces 54 that cooperate with the flexible arms 44 to move the arms 44 in an inward direction as shown by arrows 50 during movement of the fastener 16 in a fastener-installing direction 53. It is appreciated that the fixation member 14 may include greater that two arms and said arms may include a greater or fewer than four teeth in accordance with this disclosure. It is further appreciated that in addition to arms 44, pins, staples, clips, screws, rods, rivets, adhesives or other fastening mechanisms may be used to couple fixation member 14 and fastener plate 16 together.

As shown in FIGS. 1 and 2, the fastener plate 16 is formed for coupling with fasteners 42. Specifically, the fastener plate 16 includes first and second surfaces 56, 58 and apertures 60 extending between the first and second surfaces 56, 58. Each aperture 60 is positioned in general alignment with the arms 44. However, apertures 60 are a bit off-set from teeth 46 such that ramped surfaces 54 of each tooth 46 engages the plate 16 moving the arm 44 in direction 50 during installation of plate 16 onto the fixation member 14. It is appreciated that the number of apertures 60 may vary in accordance with the present disclosure based upon the number of arms 44.

As shown in FIG. 2, upon assembly of fastener plate 16 onto the fixation member 14, one face 48 of each tooth 46 engages the second surface 58 of the fastener plate 16. It is appreciated that the distance that the fastener plate 16 is positioned away from the plate 40 may vary in accordance with the present disclosure. The distance may vary depending upon the presence or absence of the spacer 18 as well as the thickness of the mask 52, as shown in FIG. 5.

Spacer 18 is illustrated in FIGS. 1 and 2. The spacer 18 is formed of a deformable material that will allow the fastener plate 16 to be pressed toward the plate 40. Preferably, the spacer 18 is formed of silicone, but it is appreciated that any number of deformable materials may be used in accordance with this disclosure. Spacer 18 includes opposite surfaces 62, 64 and apertures 66 extending between the surfaces 62, 64. The apertures 66 lay in general alignment with apertures 60 upon assembly of the apparatus 10. It is appreciated that the number of apertures 66 may vary in accordance with the present disclosure based upon the number of arms 44. In addition, it is appreciated that the spacer 18 is formed to provide a more secure connection between apparatus 10 and mask. Depending upon a variety of factors including the number of teeth on arms 42, apparatus 10 may not require the spacer 18 to adequately couple itself to the mask 52.

Figure 3:
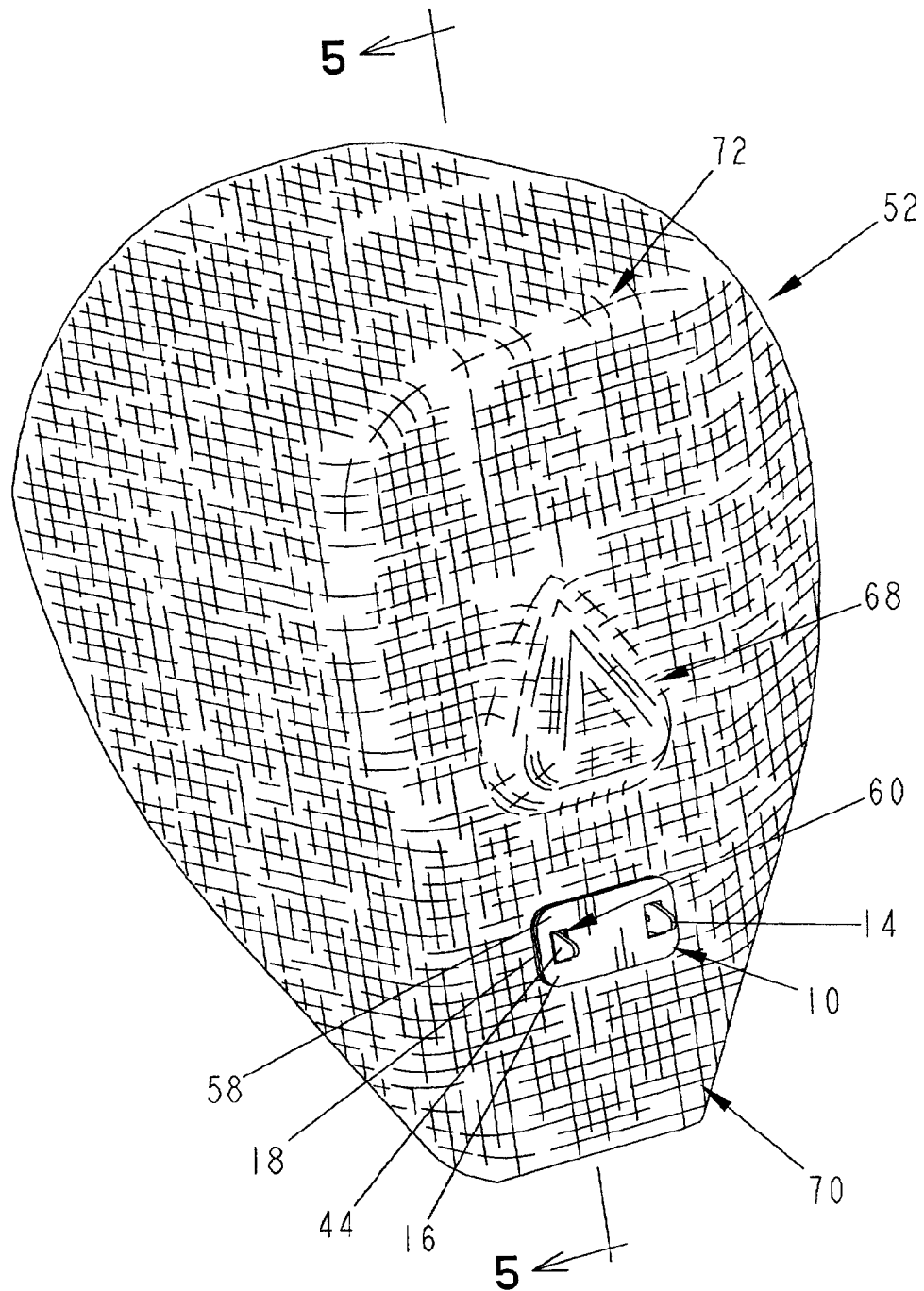
FIG. 3 is a front perspective view of the apparatus of FIG. 1 coupled to a thermoplastic mask.
Figure 4:
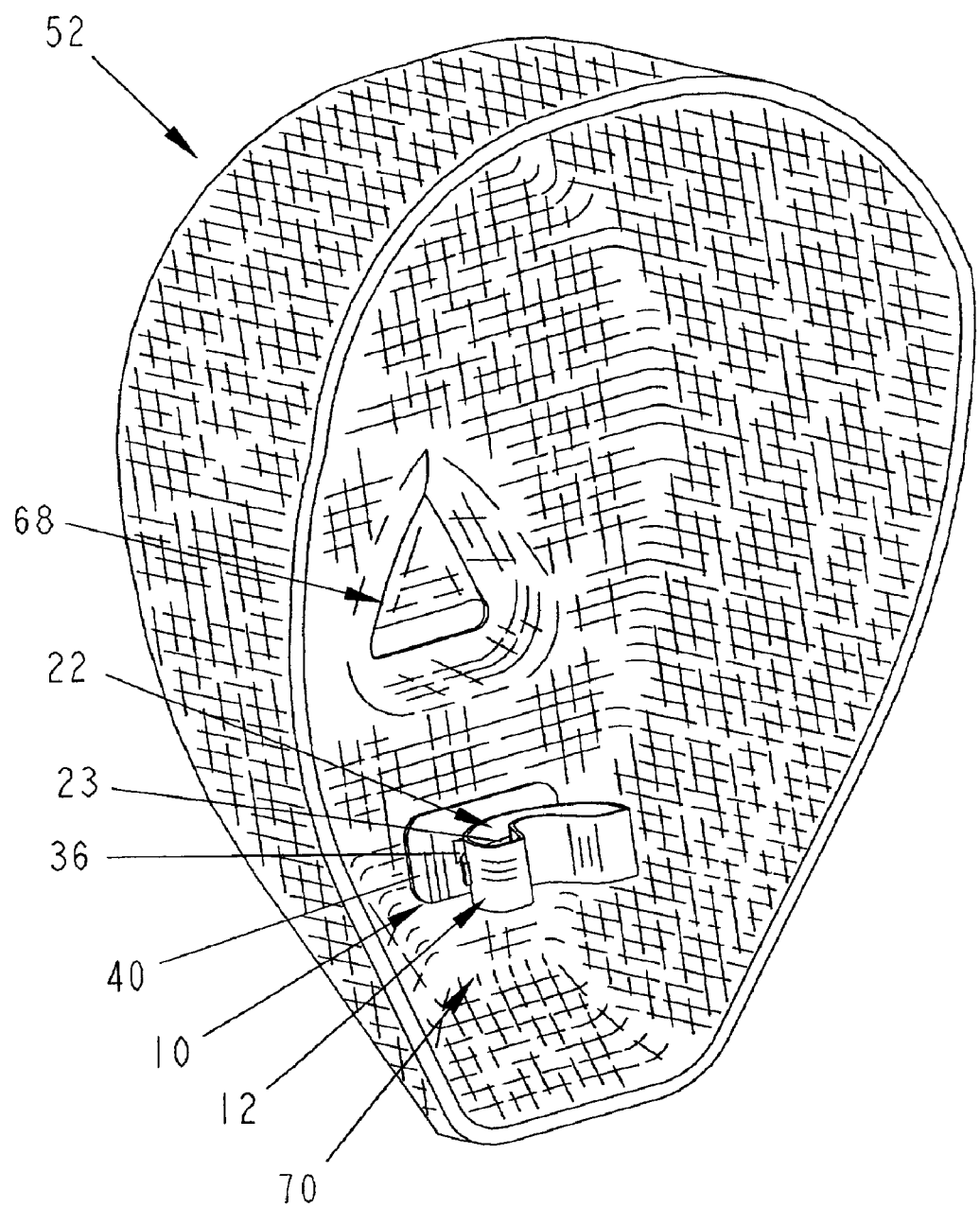
FIG. 4 is a rear perspective view of the apparatus of FIG. 1 coupled to a thermoplastic mask.
Figure 5:
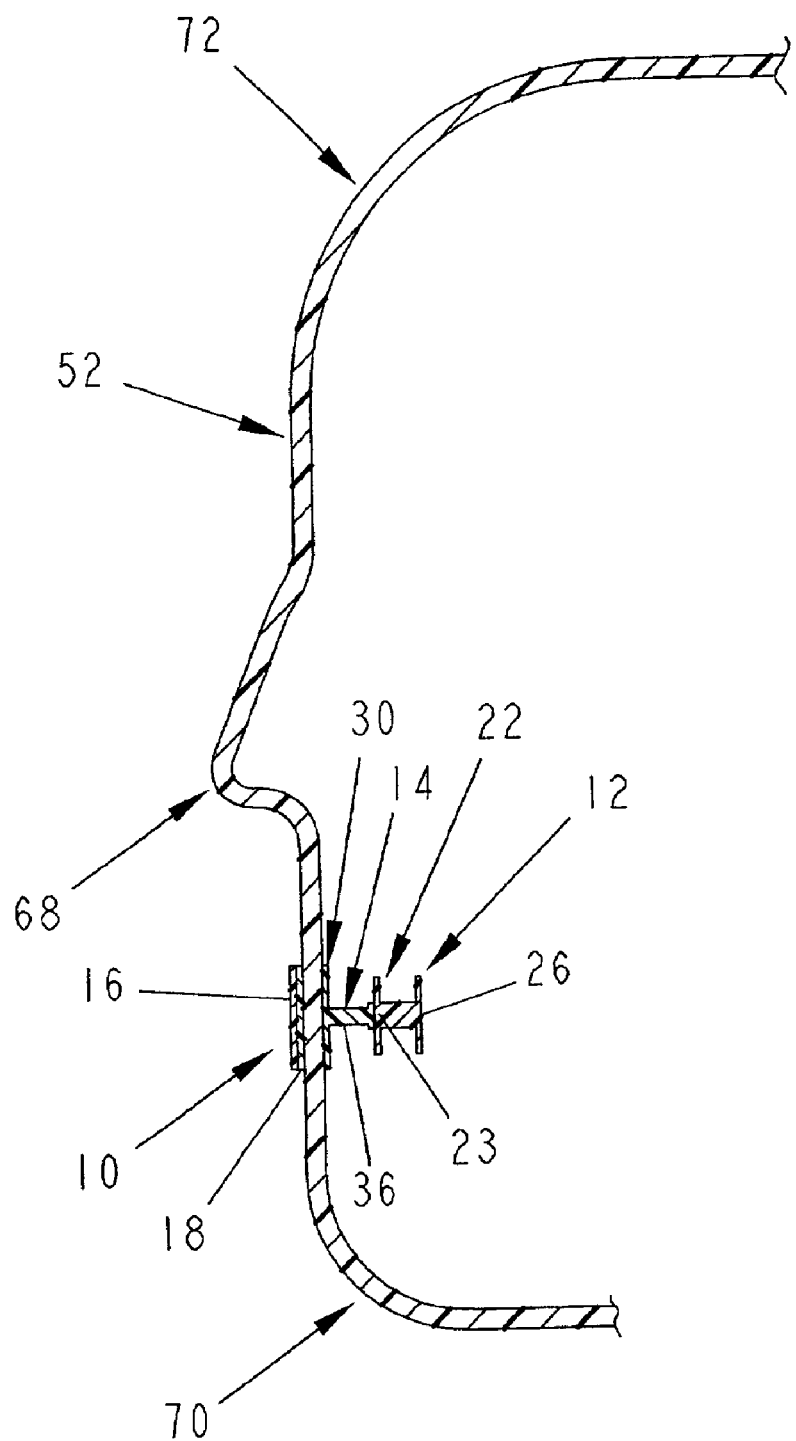
FIG. 5 is a view taken along lines 5—5 of FIG. 3.

Apparatus 10 is suitable for use with the mask 52 as shown in FIGS. 3–5. One of ordinary skill in the art appreciates that thermoplastic masks 52 have been used for patient positioning and immobilization, in for example physical therapy and radiation therapy for years. Such masks 52 are useful for placement/positioning (using fiducials directly on the thermoplastic), as well as immobilization during scanning and treatment. It is also appreciated that once formed, the mask 52 is conventionally supported by a frame (not shown). Such a frame may either allow for a single patient position, or may be formed to permit the patient to be set up in a supine flat, supine tilted, lateral, or prone position.

Mask 52 is formed of thermoplastic materials that soften under heat, are capable of being molded and shaped with hand pressure, and harden on cooling without undergoing chemical changes. A thermoplastic material, suitable for use as a mask, should soften at sufficiently low temperatures so as to form a pliable "mask" that can be formed to the patient's anatomical contours without injury due to scalding or burning of the skin. Non-limiting examples of such contours are shown in FIG. 3 and include the nose region 68, the chin region 70, and the forehead region 72. The suitable thermoplastic material should also harden as it cools to form a custom, comfortable mold for rigid fixation throughout a treatment and/or imaging process.

Suitable polymers that melt or soften at temperatures ranging from 50 degree C. to 100 degree C. include poly (ethyleneadipate), poly (epsilon-caprolactone), polyvinyl stearate, cellulose acetate, butyrate and ethyl cellulose poly (propylene oxide) containing comonomers, trans polyisoprene and cis polyisoprene based thermoplastic materials, and polycaprolactone based materials including commercially available polycaprolactone thermoplastic materials known as AQUAPLAST, SYNERGY, EZEFORM, POLYFORM and POLYFLEX II. These thermoplastic materials are available from the Rehabilitation Division of Smith & Nephew Smith & Nephew Inc., Germantown Wis.

In order to maintain a more rigid position of the mask 52 on the head of a patient (not shown), the mouthpiece member 12, which has been previously coupled to the fixation member 14, is heated to soften it and then placed in the patients' mouth. In one aspect of the invention, the mouthpiece member 12 is heated in boiling water and then placed in cooler water briefly before inserting it into the patient's mouth. Once the mouthpiece member 12 is in the patient's mouth, the patient bites down on the inner surface 23 and creates a vacuum in the mouth causing the mouthpiece member 12 to mold to the patient's dentition, or gingiva. Thus, the patient's teeth, or gingiva rest within the teeth receiving portion 22 and against the inner surface 23. Once cool, the mouthpiece member 12 is fixed relative to the patient's maxilla and the fixation member 14 that extends from mouthpiece member 12 will be in the same location relative to the patient's maxilla each time the mouthpiece member 12 is placed in the patient's mouth.

The softened thermoplastic material of the mask 52 is placed across the face of the patient such that the thermoplastic material extends over the fixation member 14, as shown in FIGS. 3–5. While the thermoplastic material cools and hardens, the fastener plate 16 is coupled to the fasteners 42 to secure the mouthpiece member 12 to the mask 52. Following cooling, the mask 52 reflects the contours of the patient's face, creating a mold. The apparatus 10 of the present invention therefore is formed to couple the mask 52 to the fixation member 14 so that the mouthpiece member 12 is in a fixed position relative to the mask 52.

Figure 6:
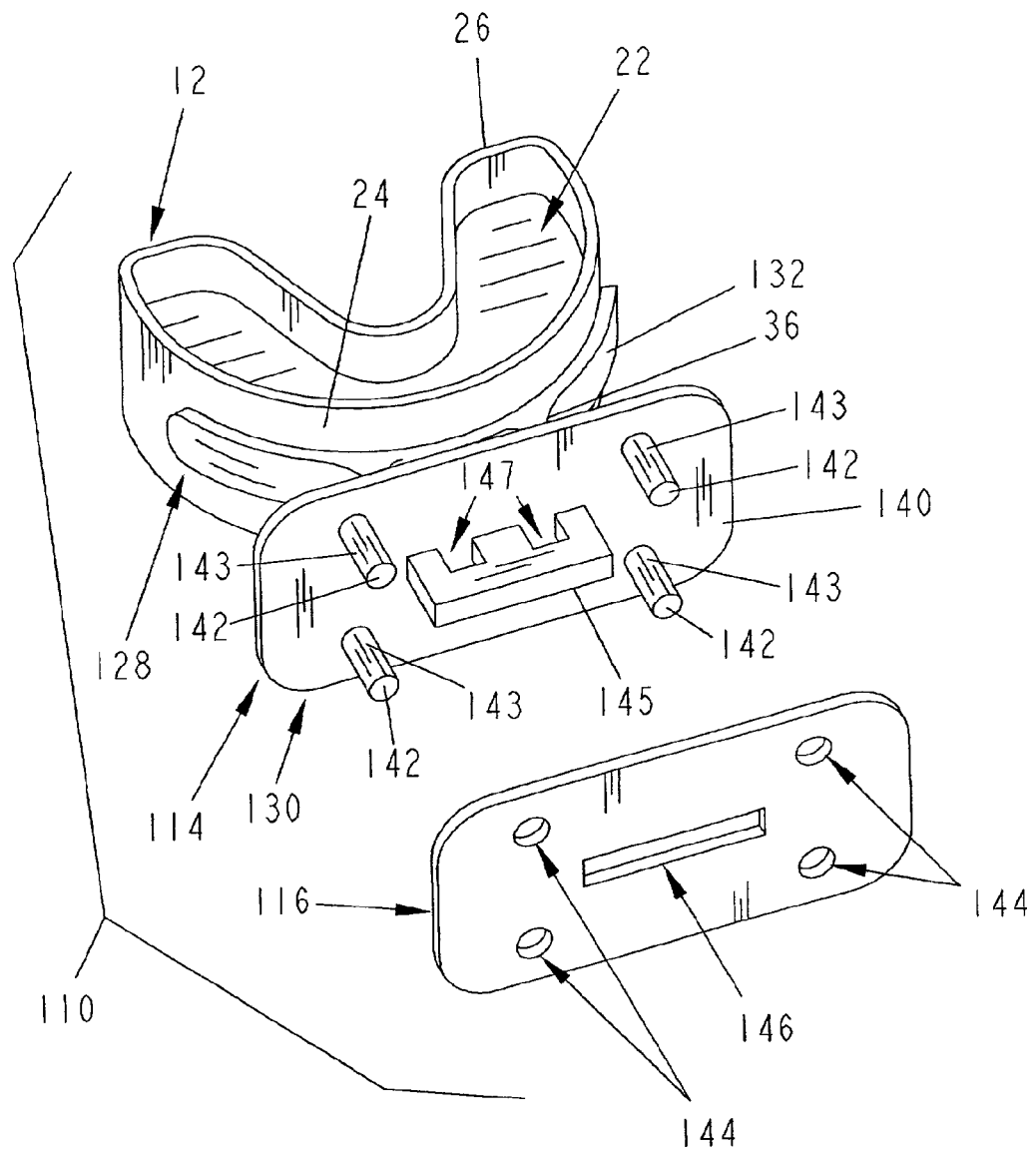
FIG. 6 is an exploded perspective view an apparatus in accordance with another embodiment of the present invention.

FIGS. 6–8 and 13–14 illustrate an aspect of the invention in the form of an apparatus 110 that is formed to maintain a more rigid position of the mask 52 on the head of a patient (not shown). Referring now to FIG. 6, apparatus 110 includes the mouthpiece member 12, a fixation member 114 extending from the mouthpiece member 12, and a fastener plate 116.

The fixation member 114 is formed of similar materials as the fixation plate 14. Fixation plate 114 is coupled to the front side 24 of the mouthpiece member 12 and is formed for attachment to the fastener plate 116. Referring to FIG. 6, the fixation member 114 includes a first end 128 coupled to mouthpiece member 12 and a second end 130 that is formed for attachment with the fastener plate 116. It is appreciated that fixation member 114 may be formed in a variety of shapes and sizes in accordance with the present invention. It is also appreciated that although the fixation member 114 is illustratively formed of a rigid plastics material, it could be constructed of a variety of materials including metal in accordance with the present disclosure.

The first end 128 of the fixation member 114 includes an attachment portion 132 that takes the general shape of the mouthpiece member 12. The attachment portion 132 is coupled to mouthpiece member 12 with a resinous material that softens when heated. A non-limiting example of a suitable material for coupling the attachment portion 132 to the mouthpiece member 12 is ELVAX® 470. It is appreciated that the attachment portion 132 may be coupled to the mouthpiece using a wide variety of commercially available adhesives or with welding (heat or ultrasonic) in accordance with this disclosure. The first end 128 of the fixation member 114 further includes extension 36 that lies between the attachment portion 132 and the second end 130 of the fixation member 114.

Figure 8:
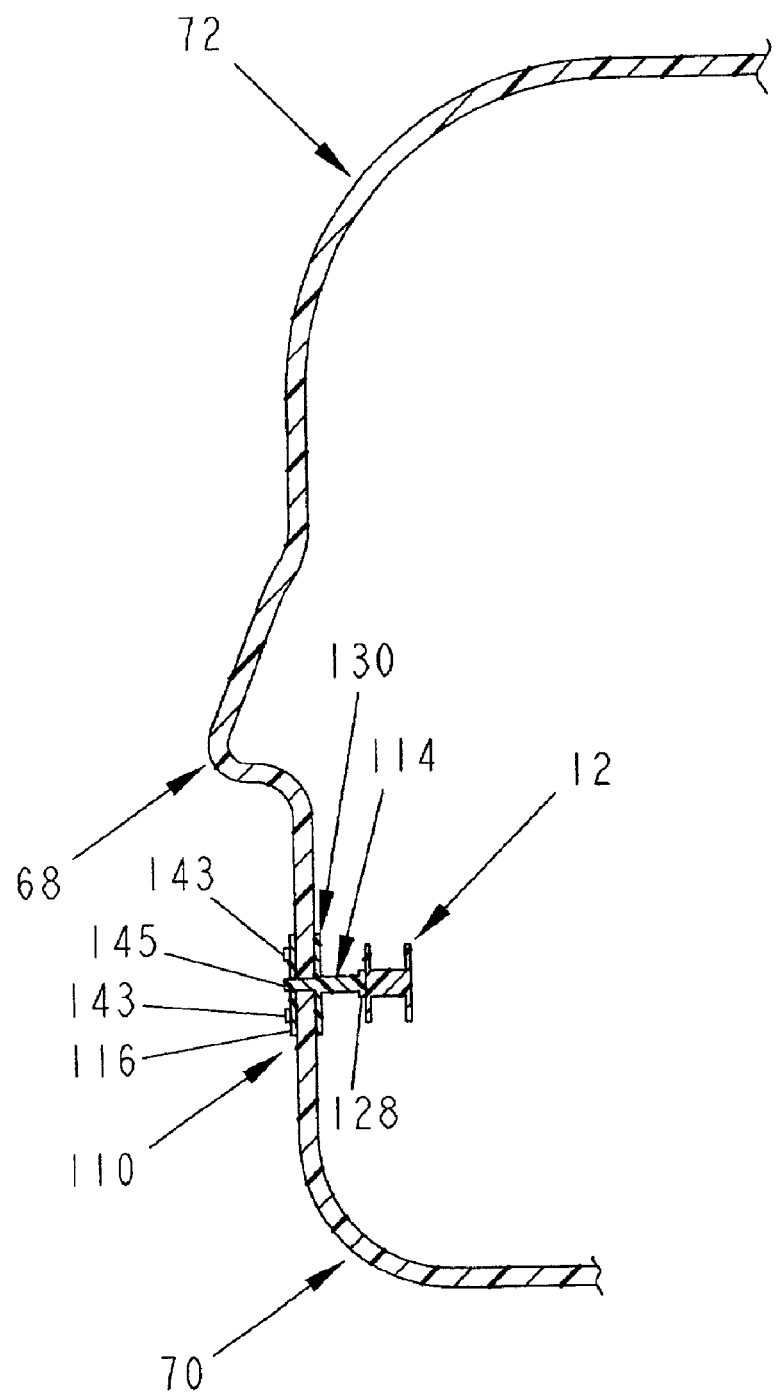
FIG. 8 is a view taken along lines 8—8 of FIG. 7.

As shown in FIGS. 6 and 8, the second end 130 of the fixation member 114 is spaced-apart from the first end 128. Referring now to FIG. 6, the second end 130 includes a plate 140 coupled to the extension 36 and fasteners 142 extending from the plate 140. Upon assembly, the fasteners 142 are locked to the fastener plate 116 in order to couple the fixation member 114 and fastener plate 116 together. Illustratively, fasteners 142 are formed as four pins 143 and a tab 145 extending from the plate 140. Each pin 143 is positioned in general alignment with a corner of the plate 140 and the tab 145 is centrally positioned between the pins 143. It is appreciated that the size, shape, and number of pins may vary in accordance with this disclosure. In addition, while tab is shown to include two openings 147, the number, size, and shape of openings through tab may vary in accordance with the disclosure. It is further appreciated that in addition to pins, rods, staples, rivets, screws, teeth, clips, adhesives or other fastening mechanisms may be used to couple fixation member 114 and fastener plate 116 together.

Figure 7:
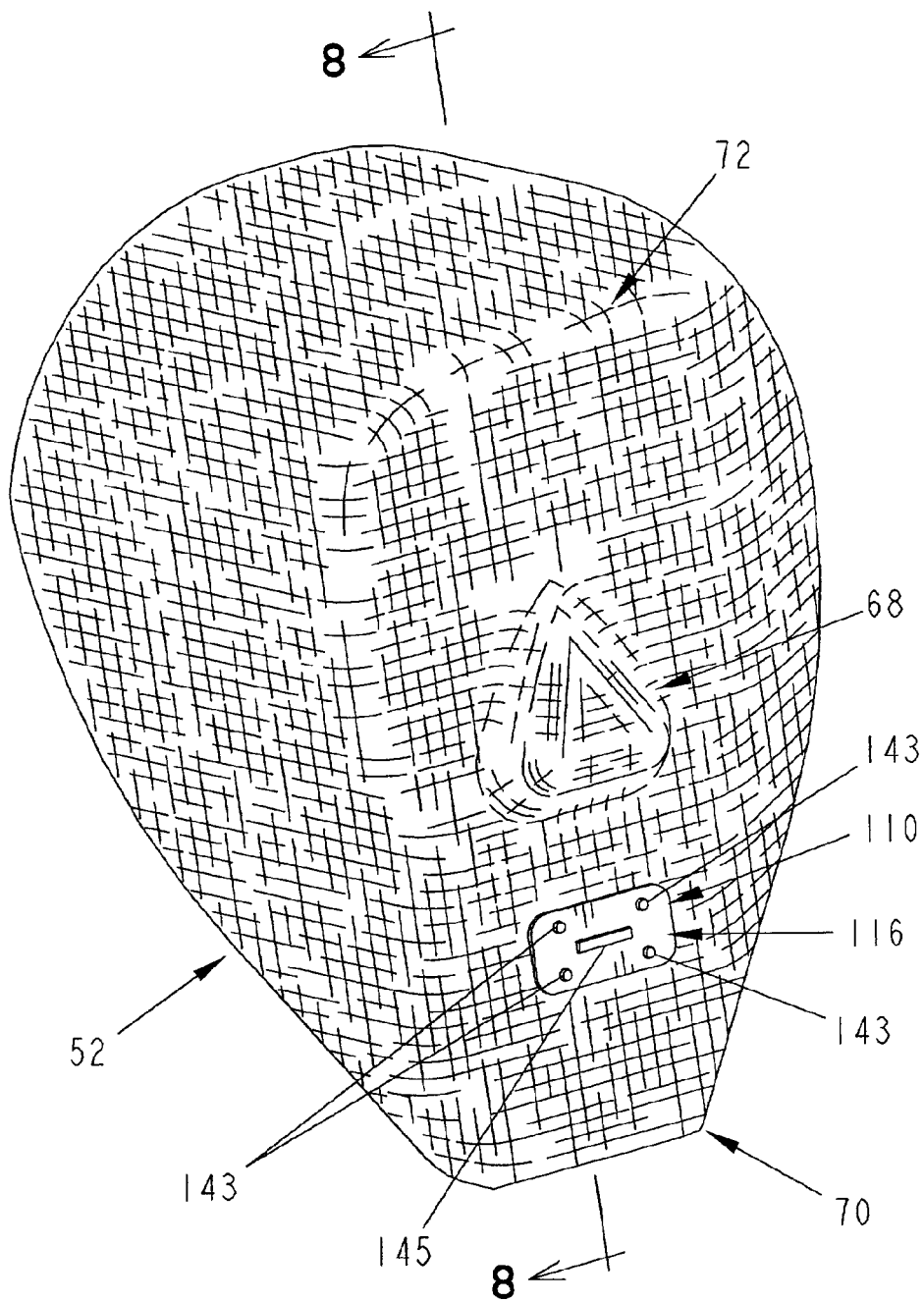
FIG. 7 is a front perspective view of the apparatus of FIG. 6 coupled to a thermoplastic mask.

Fastener plate 116 is shown in FIGS. 6 and 7. Plate 116 is formed to correspond with fasteners 142. Plate 116 includes four openings 144 that are formed for alignment with pins 143 and a slot 146 sized to receive the tab 145. As shown in FIGS. 7 and 8, upon assembly of fastener plate 116 onto the fixation member 114, each pin extends through a corresponding opening 144.

Fastener plate 116 is coupled to fasteners 142. As discussed above, it is appreciated that the plate 116 can be coupled to the fixation member 114 with an adhesive or by snapping on a clip (not shown) that extends though the openings 144 once the pins 143 and the tab 145 extend though openings 144 and slot 146 of the fastener plate 116. It is appreciated that the distance that the fastener plate 116 is positioned from the fixation member 114 may vary in accordance with the present disclosure. The distance may vary depending upon the presence or absence of the spacer 18 as well as the thickness of the mask 52 (FIG. 8). It is further appreciated that the fasteners may be alternatively formed on plate, and apertures and slot may be formed in fixation member 114 in accordance with this disclosure.

Apparatus 110 is suitable for use with the mask 52 as shown in FIGS. 7 and 8. The mouthpiece member 12 that is coupled to the fixation member 114 is softened and inserted into a patient's mouth as described above with reference to apparatus 10. The softened thermoplastic material of the mask 52 is then placed across the face of the patient such that the thermoplastic material extends over the fixation member 114. During cooling of the mask 52, the fastener plate 116 is coupled to the fasteners 142 to secure the mouthpiece member 12 to the mask 52. Following cooling and hardening of the mask 52, the mask 52 is formed to the contours of the patient's face, creating a mold as previously described. Apparatus 110 of the present invention therefore provides is fixed relative to the head of the patient each time the hardened mask 52 is applied to the patient.

Figure 9:
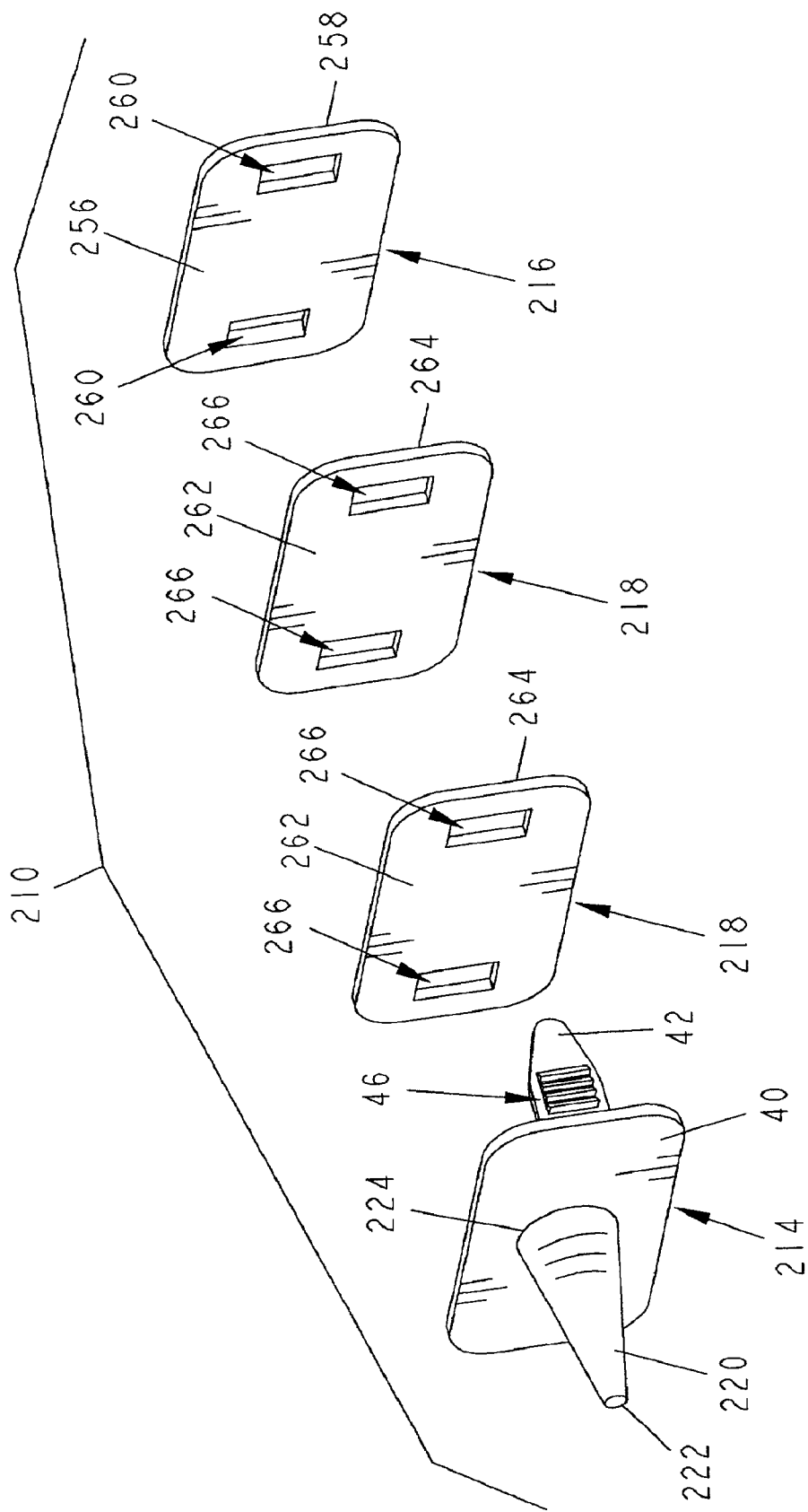
FIG. 9 is an exploded perspective view an apparatus in accordance with another embodiment of the present invention.
Figure 10:
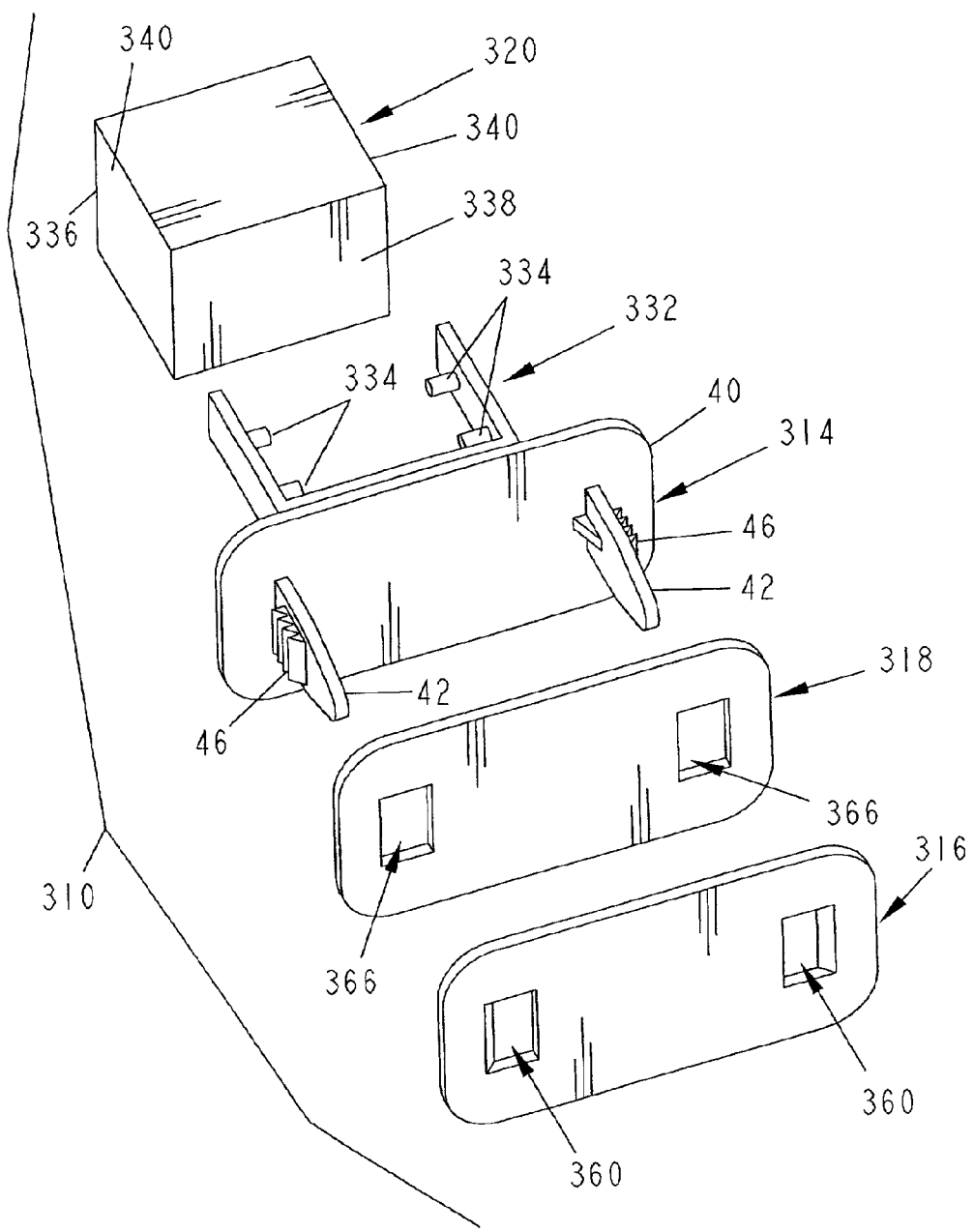
FIG. 10 is an exploded perspective view an apparatus in accordance with another embodiment of the present invention.
Figure 11:
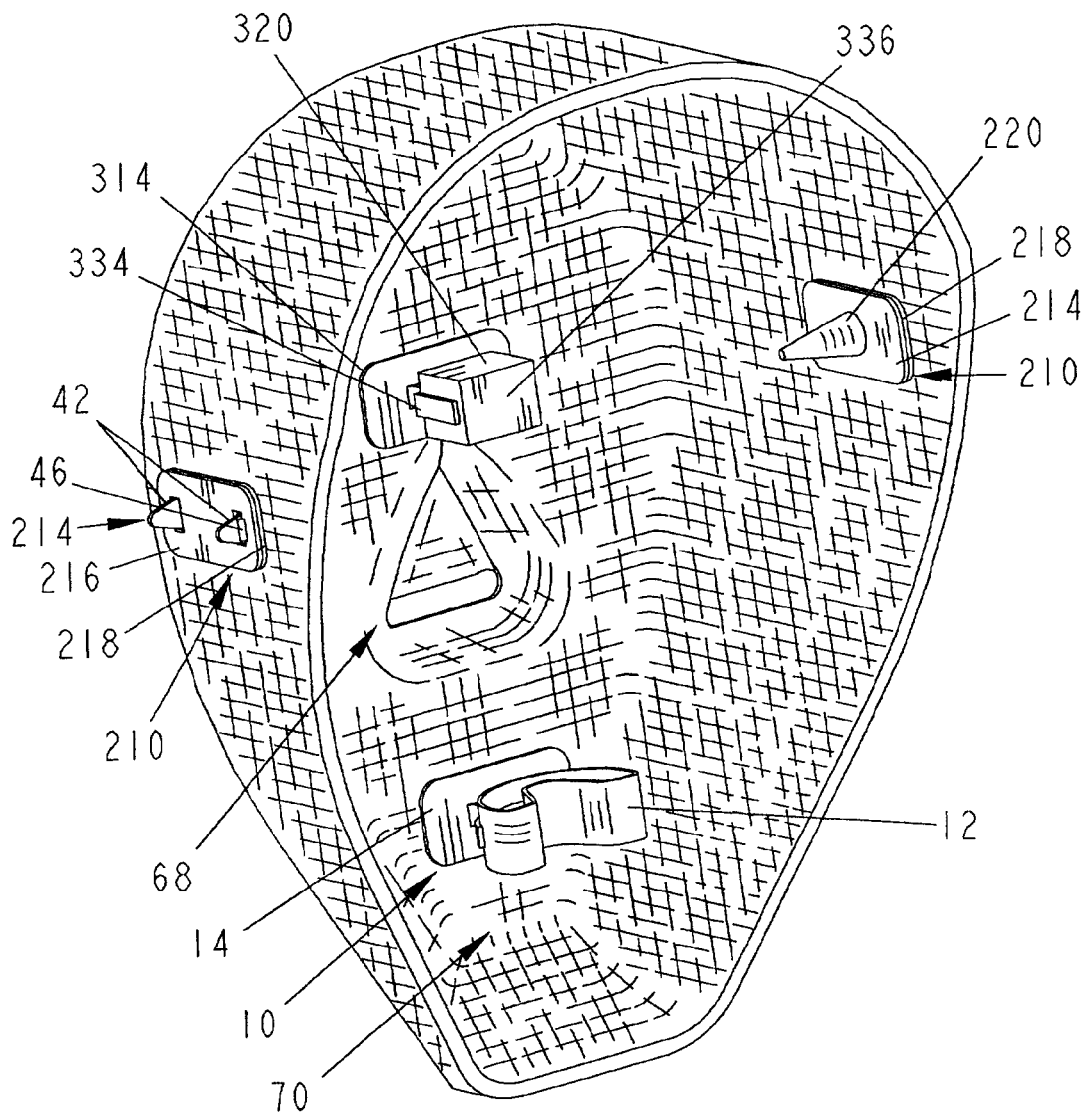
FIG. 11 is a rear perspective view of the apparatuses of FIGS. 1, 9, and 10 coupled to a thermoplastic mask.

In another aspect of the invention, an apparatus 210 is provided that is formed to couple the thermoplastic mask 52 to the internal auditory canal of the patient. As shown in FIGS. 9 and 11, apparatus 210 includes an earplug member 214, a fastener plate 216, and spacers 218. Earplug member 214 is formed from a commercially available tissue non-equivalent material, a non-limiting example of which includes carbon fiber. The earplug member 214 includes an earplug 220 that extends from plate 40. The earplug 220 is generally conical in shape and includes a first end 222 and a second end 224 positioned at the plate 40. It is appreciated that the earplug 220 may take on a variety of shapes and sizes in accordance with this disclosure. Fasteners 42 extend from plate 40 away from the earplug 220.

Fastener plate 216 is formed of materials similar to fastener plate 16. Plate 216 includes a first surface 256 facing the earplug member 214 and an opposite second surface 258. In addition, apertures 260 extend between the first and second surfaces 256, 258. It is appreciated, that apertures 260 will be aligned with fasteners 42 as discussed above with reference to apparatus 10. Additionally, it is appreciated that rather than fasteners 42, pins, rods, staples, rivets, screws, teeth, clips, adhesives or other fastening mechanisms may be used to couple fastener plate 216 and earplug member 214 together.

Spacers 218 are each formed of materials similar to spacer 18. Spacers 218 each include first and second surfaces 262, 264. In addition, apertures 266 extend between the first and second surfaces 262, 264. It is appreciated, that apertures 266 will be aligned with apertures 260 as discussed above with reference to apparatus 10.

In order to maintain a more rigid position of the mask 52 on the head of a patient (not shown), the earplug member 214 is placed in the auditory canal of a patient's ear. Once positioned, the plate 40 that lies at the end 224 of the earplug 220 will be in the same location relative to the patient's auditory canal (not shown) each time the earplug 220 is placed in the patient's ear. A spacer 218 is placed on the plate 40 so that the fasteners 42 extend through the apertures 266.

The softened thermoplastic material of the mask 52 is placed across the face of the patient such that the thermoplastic material extends over the spacer 218 that lies on the plate 40 of the earplug member 214. See, FIG. 11. As the thermoplastic material cools, the second spacer 218 is placed on the mask 52, followed by the fastener plate 216 so that the fasteners 42 extend through apertures 266, 260 respectively. The fastener plate 216 is coupled to the fasteners 42 to secure the earplug member 214 to the mask 52. Once the thermoplastic material has cooled and hardened, the mask is formed to the contours of the patient's face, creating a mold. Apparatus 210 of the present invention therefore fixes the thermoplastic mask relative to the auditory canal of a patient, preventing movement of the patient's head in the mask 52.

In another aspect of the invention, an apparatus 310 is provided that is formed to couple the thermoplastic mask 52 to the nasal bridge of a patient. Apparatus 310 is shown in FIGS. 10, 11, 13, and 14 and includes a nose block 320, a fixation member 314 formed to be coupled to the nose block 320, a fastener plate 316, and a spacer 318. Nose block 320 is formed from a commercially available resinous material that softens when heated. A non-limiting example of a suitable material for forming the nose block 320 is ELVAX® 470, an ethylene vinyl acetate copolymer and terpolymer resin, which is commercially available from E.I. DuPont de Nemours, Wilmington, Del. It is appreciated, however that the nose block 320 can also be a true custom mould in accordance with this disclosure. The nose block 320 is illustratively a block of material that includes a front face 336, a rear face 338, and sides 340 that extend between the front and rear faces 336, 338. It is appreciated that the nose block 320 may take on a variety of shapes and sizes in accordance with this disclosure.

Fixation member 314 includes plate 40, an attachment portion 332 extending from the plate 40, and fasteners 42 extending from the plate 40 away from the attachment portion 332. The fixation member 314 is formed of materials similar to fixation member 14, as previously described. Attachment portion 332 of fixation member 314 includes connectors 334 that extend generally perpendicular from arms of portion 332. The connectors 334 are coupled to the nose block 320 using ultrasonic welding. It is appreciated, however, that the attachment portion 332 of the fixation member 314 may be coupled to the nose block 320 using any number of commercially available adhesives or with heat welding in accordance with this disclosure.

Fastener plate 316 is formed of materials similar to fastener plate 16. Plate 316 includes apertures 360 that are positioned so that they will be aligned with fasteners 42 as discussed above with reference to apparatus 10, upon assembly of apparatus 310. Further, it is appreciated that rather than fasteners 42, plate 316 and the fixation member 314 may be coupled together using pins, rods, staples, rivets, screws, teeth, clips, adhesives or other fastening mechanisms in accordance with the present disclosure. Spacer 318 is formed of materials similar to spacer 18. Spacer 318 includes apertures 366 that will be aligned with apertures 360 when apparatus 310 is assembled.

In order to maintain a more rigid position of the mask 52 on the head of a patient (not shown), the nose block 320, which is coupled to fixation member 314, is heated to soften the nose block 320. The nose block 320 is then pressed on the nasal bridge of the patient to create a mold of the nasal bridge (not shown). In one aspect of the invention, the nose block 320 is heated in boiling water and then placed in cooler water briefly before placing it on the patient's nose. Once cool, the shape of the nose block 320 is fixed and the fixation member 314 that extends from nose block 320 will be in the same location relative to the patient's nasal bridge each time the nose block 320 is placed on that nasal bridge.

Once the nose block 320 is cool, the softened thermoplastic material of the mask 52 is placed across the face of the patient such that the thermoplastic material extends over the fixation member 314 that is coupled to the nose block 320. See, FIGS. 11, 13, and 14. During cooling of the thermoplastic material, the spacer 318 is placed on the mask 52, followed by the fastener plate 316 so that the fasteners 42 extend through apertures 366, 360 respectively. The fastener plate 316 is coupled to the fasteners 42 to secure the nose block 320 to the mask 52. Once the thermoplastic material has cooled and hardened, the mask 52 is formed to the contours of the patient's face, creating a mold. The apparatus 310 of the present invention therefore fixes the thermoplastic mask relative to the nasal bridge of a patient, preventing movement of the patient's head in the mask 52.

Figure 12:
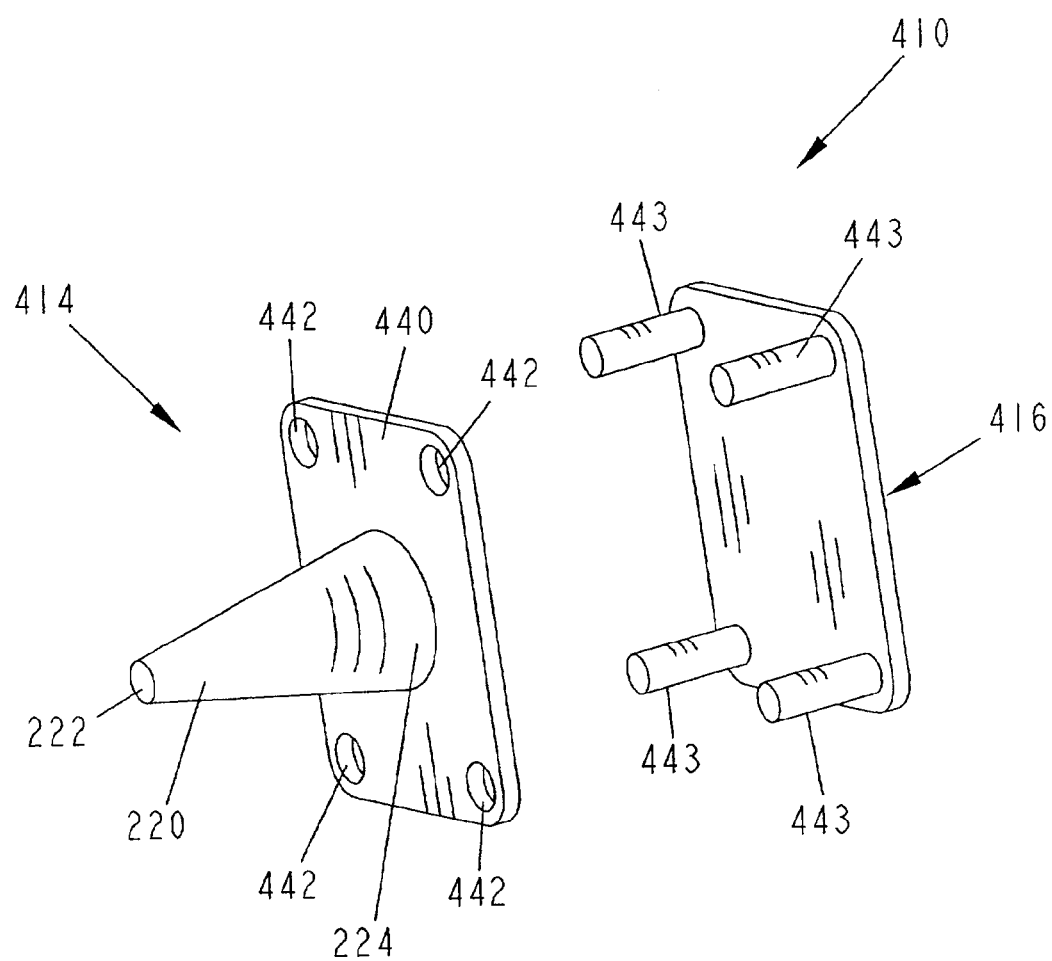
FIG. 12 is an exploded perspective view of an apparatus in accordance with another embodiment of the present invention.
Figure 13:
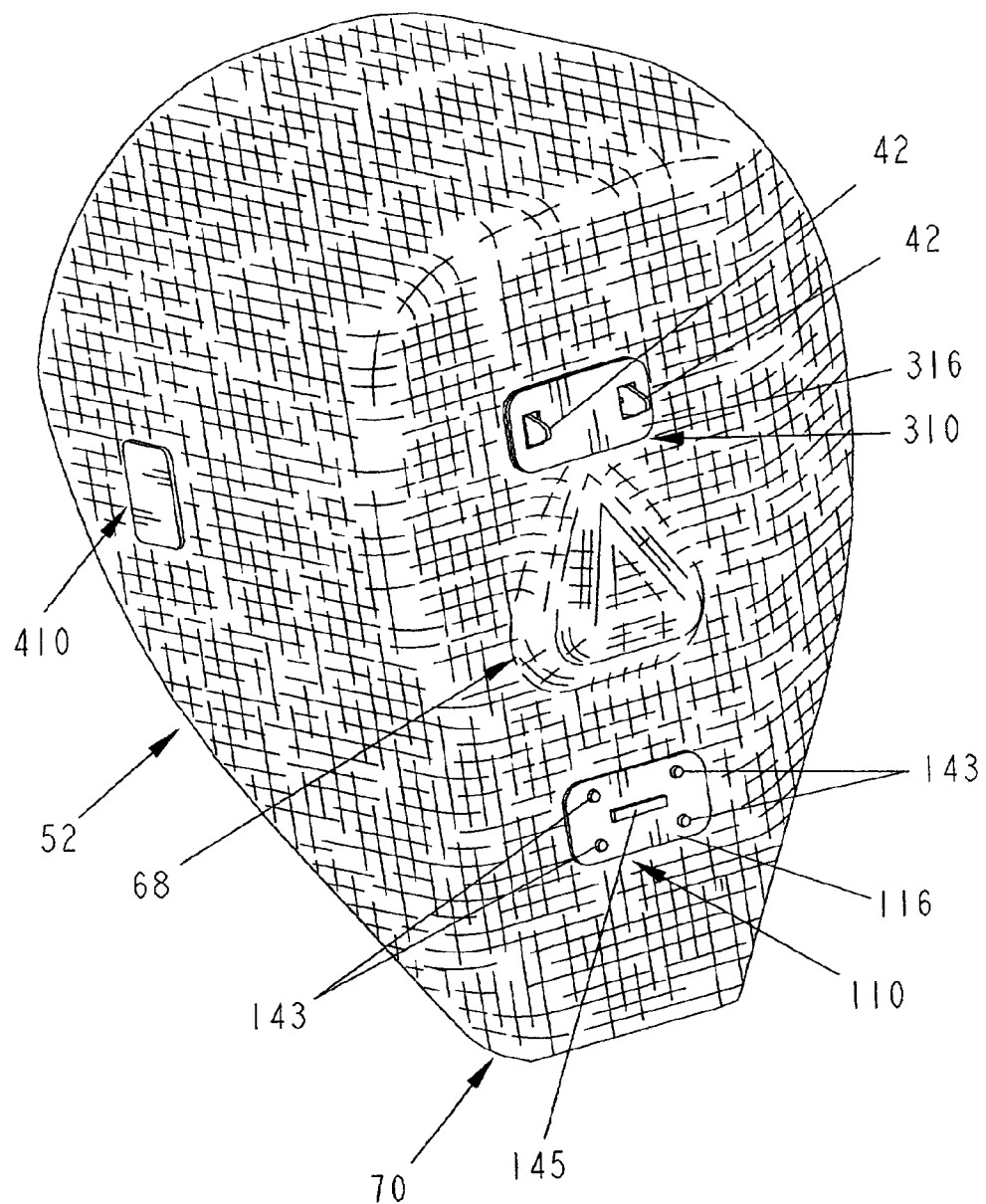
FIG. 13 is a front perspective view of the apparatuses of FIGS. 6, 10, and 12 coupled to a thermoplastic mask.
Figure 14:
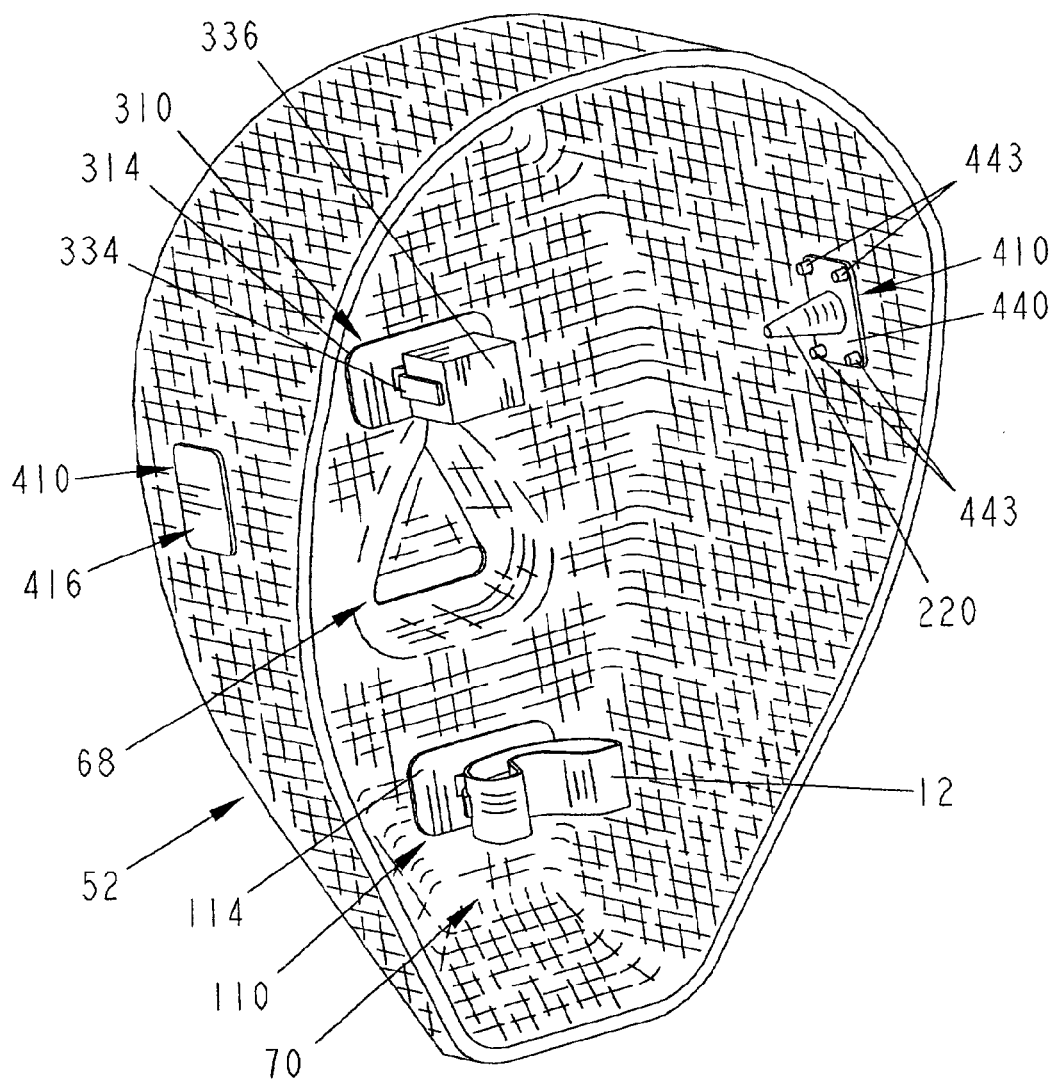
FIG. 14 is a rear perspective view of the apparatus of FIGS. 6, 10, and 12 coupled to a thermoplastic mask.

In another aspect of the invention, an apparatus 410 is provided that is formed to couple the thermoplastic mask 52 to the internal auditory canal of the patient. As shown in FIGS. 12–14, apparatus 410 includes an earplug member 414 and a fastener plate 416. Earplug member 414 is formed from a commercially available tissue non-equivalent material, a non-limiting example of which includes carbon fiber. The earplug member 414 includes the earplug 220 that extends from a plate 440. The plate includes four apertures 442.

Fastener plate 416 is formed of materials similar to fastener plate 16. Plate 416 includes four posts 443. The posts 443 are positioned for alignment with apertures 442. It is appreciated that the number and locations of posts can vary in accordance with the present disclosure so long as they are in alignment with the apertures 442. Further, it is appreciated that rather than posts 443, the fastener plate 416 and the earplug member 414 may be coupled together using pins, rods, staples, rivets, screws, teeth, clips, adhesives or other fastening mechanisms in accordance with the present disclosure.

In order to maintain a more rigid position of the mask 52 on the head of a patient (not shown), the earplug 220 is placed in the auditory canal of a patient's ear.

Once positioned, the plate 440 that lies at that end 224 of the earplug 220 will be in the same location relative to the patient's auditory canal each time the earplug 220 is placed in the patient's ear.

The softened thermoplastic material of the mask 52 is placed across the face of the patient such that the thermoplastic material extends over the plate 440. See, FIGS. 13 and 14. As the thermoplastic material cools, the fastener plate 416 is placed on the mask 52 so that the pins 443 extend through apertures 442. The fastener plate 416 is coupled to the pins 443 to secure the earplug member 414 to the mask 52. It is appreciated that the fastener plate 416 may be coupled to plate 440 using a variety of adhesives, fasteners, etc. Once the thermoplastic material has cooled and hardened, the mask 52 is formed to the contours of the patient's face, creating a mold. Apparatus 410 of the present invention therefore fixes the thermoplastic mask relative to the auditory canal of a patient, preventing movement of the patient's head in the mask 52.

As shown in FIGS. 11, 13, and 14 it is appreciated that one or a combination of more than one apparatus 10, 110, 210, 310, 410 may be used to fix the thermoplastic mask relative to the patient's head in accordance with this disclosure.

Figure 15:
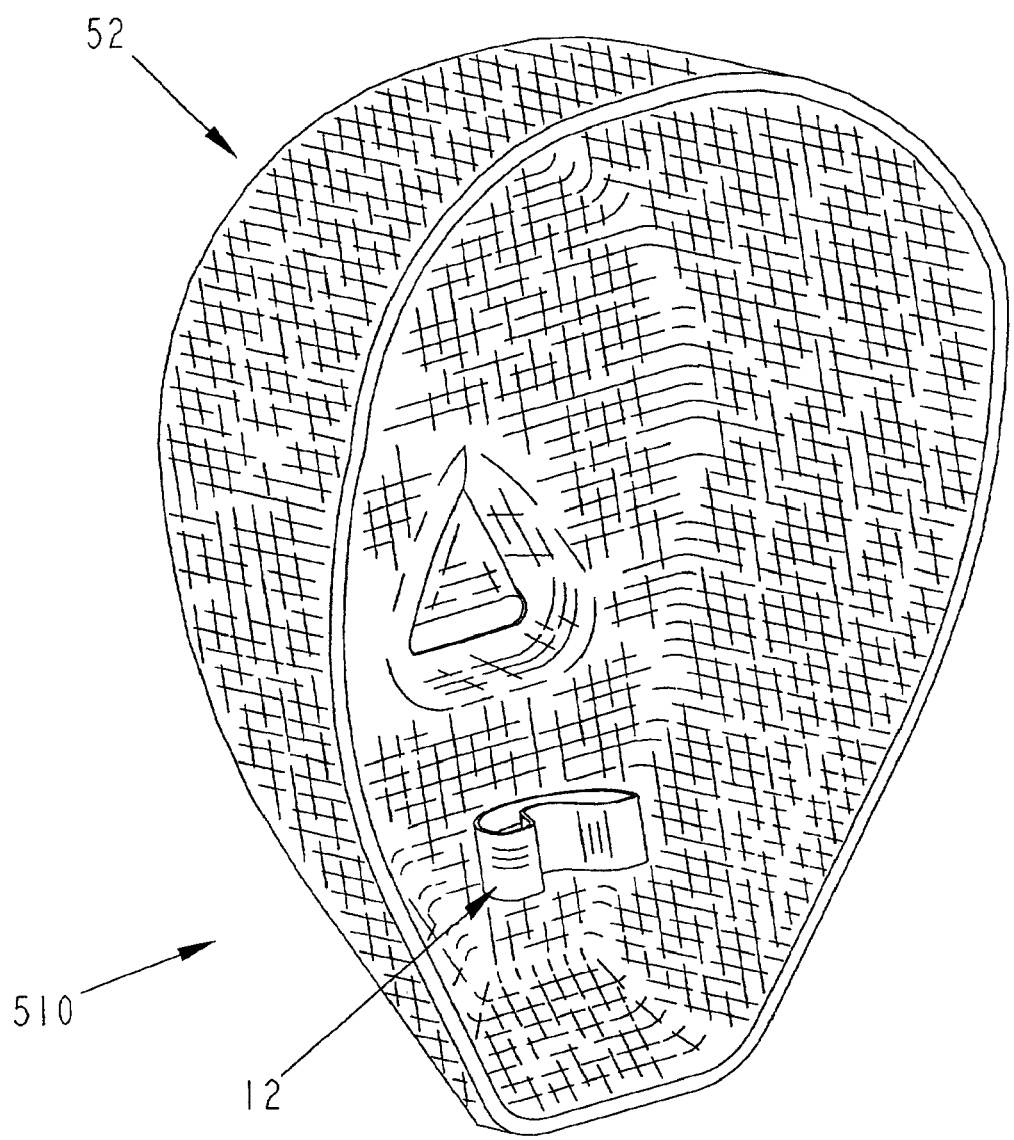
FIG. 15 is a rear perspective view of an apparatus in accordance with another embodiment of the present invention.

FIG. 15 illustrates aspects of the invention in the form of assembly 510 that includes a mask that is formed to be fixed relative to cranio facial bones, i.e. maxilla.

Assembly 510 includes mouthpiece member 12 that is fixed to the mask 52 with an adhesive. Suitable adhesives are resinous materials that soften when heated. A non-limiting example of a suitable adhesive material is ELVAX® 470, an ethylene vinyl acetate copolymer and terpolymer resin, which is commercially available from E.I.

DuPont de Nemours, Wilmington, Del. It is appreciated, however that the adhesive may be selected of any number of commercially available adhesives. In addition, it is appreciated that pins, rods, staples, rivets, screws, teeth, clips, or any number of fastening mechanisms may be used to couple the mouthpiece member 12 and mask 52 together in accordance with the present disclosure.

In order to maintain a more rigid position of the mask 52 relative to the maxilla, the mouthpiece member 12 is heated to soften it and then placed in the patients' mouth. In one aspect of the invention, the mouthpiece member 12 is heated in boiling water and then placed in cooler water briefly before inserting it into the patient's mouth. Once the mouthpiece member 12 is in the patient's mouth, the patient bites down on the inner surface 23 and creates a vacuum in the mouth causing the mouthpiece member 12 to mold to the patient's dentition, or gingiva. Thus, the patient's teeth, or gingiva rest within the teeth receiving portion 22 and against the inner surface 23.

The softened thermoplastic material of the mask 52 is placed across the face of the patient such that the thermoplastic material extends over the warm front side 24 of the mouthpiece member 12. While the thermoplastic material cools and hardens, the warm adhesive is applied to the front side 24 and mask 52 to secure the mouthpiece member 12 to the mask 52. Following cooling, the mask 52 reflects the contours of the patient's face, creating a mold. The assembly 510 of the present invention therefore fixes the thermoplastic mask relative to the maxilla of a patient, preventing movement of the patient's head in the mask 52.

Figure 16:
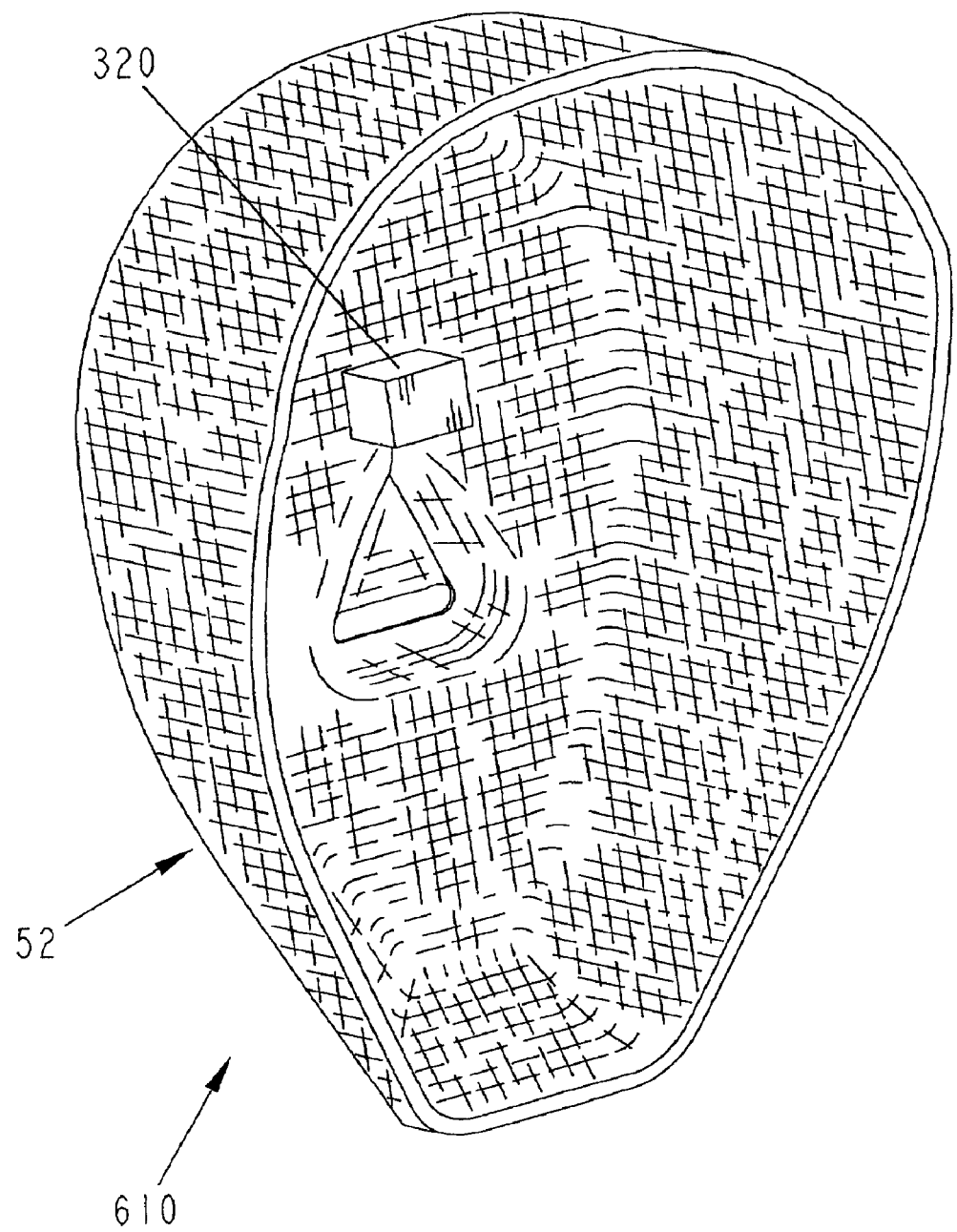
FIG. 16 is a rear perspective view of an apparatus in accordance with another embodiment of the present invention.
Figure 17:
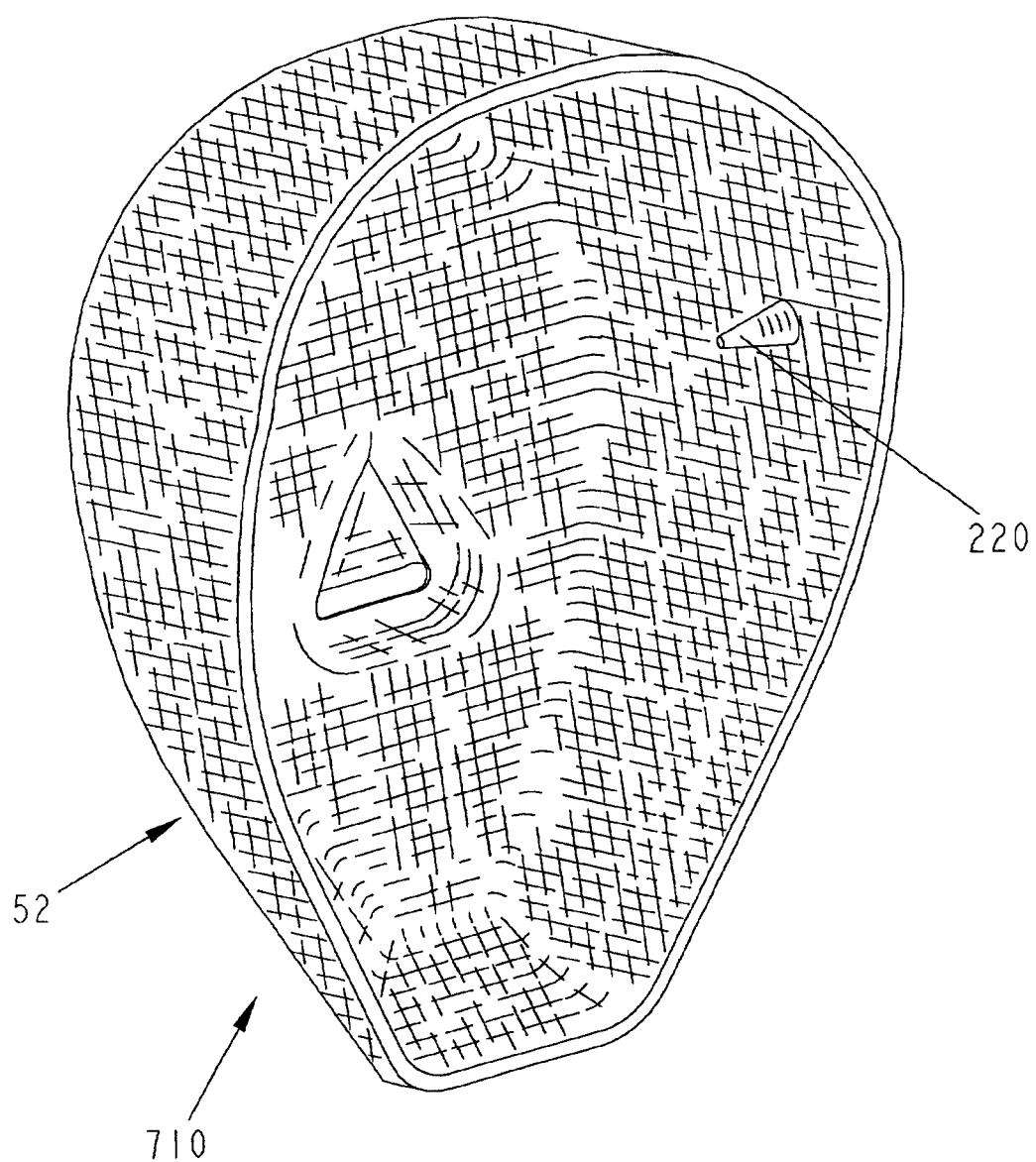
FIG. 17 is a rear perspective view of an apparatus in accordance with another embodiment of the present invention.

In addition, as illustrated in FIGS. 16 and 17 respectively, it is appreciated that nose block 320 and earplug 222 may be coupled directly to mask 52 in a manner similar to mouthpiece member 12 as described above with reference to assembly 510 to form assemblies 610, 710. It is further appreciated that pins, rods, staples, rivets, screws, teeth, clips, or any number of fastening mechanisms may be used to couple the nose block 320 and earplug 222 to their respective mask 52 in accordance with the present disclosure.

Although the invention has been described in detail with reference to a preferred embodiment, variations and modifications exist within the scope and spirit of the invention as described and defined.

What is claimed is:

1. An apparatus formed to fix a thermoplastic mask to a patient, the apparatus comprising:
    a member having a teeth-receiving portion formed to be positioned adjacent to a cranio facial bone of the patient,
    a generally rigid fixation member coupled to the member, the fixation member including a plate and a fastener, and
    a distinct fastener plate formed for coupling with the fastener to couple the mask to the fixation member so that the member is in a fixed position relative to the mask.

2. An apparatus formed to fix a thermoplastic mask to a patient, the apparatus comprising:
    a member formed to be positioned adjacent to a cranio facial bone of the patient,
    a generally rigid fixation member coupled to the member and including an attachment portion coupled to the member and a plate spaced-apart from the attachment portion, and
    a distinct fastener plate formed to couple the mask to the fixation member so that the member is in a fixed position relative to the mask.

3. The apparatus of claim 2 wherein the fixation member further includes fasteners extending from the plate for engagement with the fastener plate.

4. The apparatus of claim 2 wherein the fasteners include teeth.

5. The apparatus of claim 2 wherein the fasteners include a tab and posts extending from the plate.

6. The apparatus of claim 2 further comprising a spacer positioned to lie between the fixation member and the fastener plate.

7. The apparatus of claim 2 wherein the member is a mouthpiece.

8. The apparatus of claim 2 wherein the fixation member includes a plate and at least one fastener extending from the plate, the fastener cooperating with the fastener plate to couple the member to the fastener plate.

9. The apparatus of claim 8 wherein the at least one fastener includes teeth.

10. The apparatus of claim 8 further comprises at least one spacer positioned to lie between the fixation member and the fastener plate.

11. An assembly formed to immobilize a patient's skull during a medical procedure, the assembly comprising:

a thermoplastic mask, a generally rigid fixation member including an attachment portion, an extension extending from the attachment portion, and a plate coupled to the extension, the mask being formed to extend across the plate, and a mouthpiece member coupled to the attachment portion of the fixation member in order that the mouthpiece member be coupled to the thermoplastic mask.

12. The assembly of claim 11 wherein the mask and mouthpiece member are coupled together with the fixation member and a fastener plate.

13. An apparatus formed to fix a thermoplastic mask to a patient, the apparatus comprising:

a mouthpiece member, a fixation member coupled to the mouthpiece member, the fixation member including a generally rigid plate and at least one fastener extending away from the plate, and a distinct fastener plate formed for attachment with the at least one fastener so that the mask is coupled between the plate and the fastener plate.

14. The apparatus of claim 13 wherein the at least one fastener includes teeth.

15. The apparatus of claim 14 wherein the fixation member includes two fasteners.

* * * * *